(12) United States Patent
Lemoine et al.

(10) Patent No.: US 7,332,154 B2
(45) Date of Patent: Feb. 19, 2008

(54) DEODORANT COSMETIC COMPOSITION COMPRISING A COMBINATION OF ZINC GLUCONATE AND AN ANTIPERSPIRANT ALUMINUM SALT

(75) Inventors: Cyril Lemoine, Puiseux-en-France (FR); Nathalie Beau, Eragny-sur-Oise (FR); Estelle Prud'Homme, Paris (FR)

(73) Assignee: L'Oreal S.A., Paris (FR)

( * ) Notice: Subject to any disclaimer, the term of this patent is extended or adjusted under 35 U.S.C. 154(b) by 588 days.

(21) Appl. No.: 11/009,269

(22) Filed: Dec. 13, 2004

(65) Prior Publication Data
US 2005/0180935 A1    Aug. 18, 2005

Related U.S. Application Data

(60) Provisional application No. 60/534,408, filed on Jan. 7, 2004.

(30) Foreign Application Priority Data
Dec. 12, 2003   (FR) .................................. 03 51034

(51) Int. Cl.
A61Q 15/00     (2006.01)
A61K 8/00      (2006.01)
A61K 8/04      (2006.01)
(52) U.S. Cl. .................... 424/65; 424/68; 424/400; 424/401
(58) Field of Classification Search ................ 424/65, 424/68, 400, 401
See application file for complete search history.

(56) References Cited

U.S. PATENT DOCUMENTS

| | | | |
|---|---|---|---|
| 3,792,068 | A | 2/1974 | Luedders et al. |
| 4,822,596 | A | 4/1989 | Callingham et al. |
| 4,904,463 | A | 2/1990 | Johnson et al. |
| 5,643,559 | A | 7/1997 | Eigen et al. |
| 6,403,067 | B1 | 6/2002 | Schamper et al. |
| 6,426,061 | B1 | 7/2002 | Li et al. |
| 6,632,421 | B2 | 10/2003 | Ascione et al. |

FOREIGN PATENT DOCUMENTS

| | | |
|---|---|---|
| DE | 101 37 901 A1 | 12/2002 |
| EP | 0 768 080 B1 | 4/1997 |
| FR | 2 815 856 | 5/2002 |
| JP | 62-289512 A | 12/1987 |
| JP | 3-95111 A | 4/1991 |
| WO | WO 97/14399 A1 | 4/1997 |
| WO | WO 97/44010 | 11/1997 |
| WO | WO 00/68369 | 11/2000 |
| WO | WO 01/52804 A1 | 7/2001 |
| WO | WO 01/89452 A2 | 11/2001 |
| WO | WO 01/99376 A2 | 12/2001 |

OTHER PUBLICATIONS

Patent Abstracts of Japan, Abstract for JP 62-289512, 1 page.
Patent Abstracts of Japan, Abstract for JP 03-095111, 1 page.
English language Derwent Abstract of DE 101 37 901 A1, Dec. 5, 2002.
English language Derwent Abstract of FR 2 815 856, May 3, 2002.
Charles Fox, "An Introduction to Multiple Emulsions," Cosmetics & Toiletries, vol. 101, No. 11, Nov. 1986, pp. 101-112.

*Primary Examiner*—Shelley A. Dodson
(74) *Attorney, Agent, or Firm*—Finnegan, Henderson, Farabow, Garrett & Dunner LLP

(57) ABSTRACT

The disclosure provides deodorant cosmetic compositions comprising:
(a) zinc gluconate, and
(b) at least one antiperspirant aluminum salt;
wherein the zinc gluconate/antiperspirant aluminum salt weight ratio ranges from 1/100 to 10/1. The disclosure also provides cosmetic processes for treating human perspiration and human underarm odors with these compositions and aerosols comprising these compositions.

29 Claims, No Drawings

DEODORANT COSMETIC COMPOSITION COMPRISING A COMBINATION OF ZINC GLUCONATE AND AN ANTIPERSPIRANT ALUMINUM SALT

This application claims the benefit of U.S. Provisional Application No. 60/534,408, filed Jan. 7, 2004, hereby incorporated by reference.

The disclosure provides deodorant cosmetic compositions comprising:
 (a) zinc gluconate, and
 (b) at least one antiperspirant aluminum salt;
wherein the zinc gluconate/aluminum salt weight ratio ranges from 1/100 to 10/1.

The disclosure also provides cosmetic processes for treating human perspiration and human underarm odors with these compositions. In addition, the disclosure provides aerosol devises comprising the compositions and a means for distributing the deodorant compositions.

In the cosmetic field, it is a well-known practice to use, in topical applications, deodorant products containing antiperspirant, bactericidal, and odor absorbent active substances to reduce and even eliminate generally unpleasant underarm odors.

Bactericides inhibit the growth of the skin flora responsible for underarm odors. They have the drawback of not being active on the sweat odor already developed. A commonly used bactericidal product is Triclosan (2,4,4'-trichloro-2'-hydroxydiphenyl ether), which has the drawback of considerably modifying the ecology of the skin flora and of being inhibited by certain compounds such as, for example, nonionic surfactants, which are commonly used in the formulation of cosmetic compositions. Furthermore the insoluble nature of Triclosan in water does not allow it to be incorporated into essentially aqueous formulations.

Antiperspirant substances limit the flow of sweat and generally comprise aluminum salts. Their efficacy as deodorants is limited when they are used alone. Furthermore, in high concentrations, these substances may irritate the skin.

EP Patent No. 768,080 discloses aqueous deodorant compositions, including water/silicone emulsions containing as odor-absorbing active agents water-soluble zinc salts, for example, zinc pyrrolidonecarboxylate, zinc sulfate, zinc chloride, zinc lactate, zinc gluconate, and zinc phenolsulfonate. These compositions have the drawback of not having a fully satisfactory deodorant efficacy when used alone.

U.S. Pat. No. 6,426,061 also discloses compositions for combating the development of human skin perspiration odors, comprising the combination of the following active agents: (1) an androgen receptor inhibitor, such as resveratrol, epigallocatechin 3-gallate, and flufenamic acid; (2) an anti-DHT active agent, such as zinc salts, for example, zinc sulfate; (3) an inhibitor of odor-bearing proteins; (4) an antiperspirant aluminum salt; and (5) an antimicrobial agent such as chlorhexidine gluconate or chlorhexidine diacetate. These compositions have the drawback of using antimicrobial agents that are particularly active on the cutaneous flora.

PCT patent application WO 01/52804 discloses deodorant compositions based on antiperspirant salts and proposes adding transition metal-chelating agents. These formulations have the drawbacks of being potentially ecotoxic and posing environmental problems.

PCT patent application WO 01/99376 also discloses deodorant compositions containing arylsulfatase inhibitors, such as aluminum salts and zinc gluconate. An example of an antiperspirant stick containing 20% by weight of aluminum chlorohydrate and 0.1% of zinc gluconate is described. This type of composition has the drawback of producing a high level of white residue on the skin after application.

Thus, there is a need for novel cosmetic compositions comprising a deodorant system with an efficacy higher than that of antiperspirant salts and than that of zinc gluconate salts used alone, and which do not have the drawbacks of the deodorant products of the prior art mentioned above.

In one embodiment, applicants have discovered a composition obtained by using a combination of zinc gluconate and an antiperspirant aluminum salt in a zinc gluconate/aluminum salt weight ratio ranging from 1/100 to 10/1.

In one embodiment, Applicants have discovered that this combination may have a synergistic effect on reducing the odor intensity compared with the active agents used individually.

Applicants have also discovered that this combination may be formulated in cosmetically acceptable deodorant compositions with low levels of visible residue on the skin upon application and after drying of the composition after application that are comparable with the deodorant products currently on the market.

In one aspect, the disclosure provides deodorant cosmetic compositions comprising:
 (a) zinc gluconate, and
 (b) at least one antiperspirant aluminum salt; wherein the zinc gluconate/aluminum salt weight ratio ranges from 1/100 to 10/1. In some embodiments, the zinc gluconate/aluminum salt weight ratio ranges from 1/20 to 5/1.

The disclosure also provides cosmetic processes for treating human perspiration and human underarm odors using this composition.

As used herein, the term "deodorant composition" means any composition capable of reducing the flow of sweat and of masking, absorbing, improving and/or reducing the unpleasant odor resulting from the decomposition of human sweat by bacteria.

As used herein, the term "antiperspirant aluminum salt" means any salt or any aluminum complex that has the effect of reducing or limiting the flow of sweat.

Aluminum salts that may be used include aluminum halohydrates; aluminum zirconium halohydrates; and complexes of zirconium hydroxychloride and aluminum hydroxychloride with an amino acid, such as those described in patent U.S. Pat. No. 3,792,068, which are commonly known as "ZAG complexes."

Specific aluminum salts include aluminum chlorohydrate in activated or unactivated form, aluminum chlorohydrex, aluminum chlorohydrex polyethylene glycol complex, aluminum chlorohydrex propylene glycol complex, aluminum dichlorohydrate, aluminum dichlorohydrex polyethylene glycol complex, aluminum dichlorohydrex propylene glycol complex, aluminum sesquichlorohydrate, aluminum sesquichlorohydrex polyethylene glycol complex, aluminum sesquichlorohydrex propylene glycol complex, and aluminum sulfate buffered with sodium aluminum lactate.

Aluminum zirconium double salts include aluminum zirconium octachlorohydrate, aluminum zirconium pentachlorohydrate, aluminum zirconium tetrachlorohydrate, and aluminum zirconium trichlorohydrate.

Complexes of zirconium hydroxychloride and of aluminum hydroxychloride with an amino acid are generally known as ZAG when the amino acid is glycine. ZAG complexes include aluminum zirconium octachlorohydrex glycine, aluminum zirconium pentachlorohydrex glycine, aluminum zirconium tetrachlorohydrex glycine, and aluminum zirconium trichlorohydrex glycine complexes.

For example, aluminum chlorohydrate in activated or unactivated form may be used.

The antiperspirant aluminum salts may be present in the compositions a proportion ranging from about 0.5% to 25% by weight relative to the total weight of the composition.

Zinc gluconate may be present in the compositions in a proportion ranging from about 0.1% to 10% by weight, such as from 0.1% to 7% by weight, relative to the total weight of the composition.

The deodorant compositions intended for cosmetic use may be in the form of lotions, creams or fluid gels distributed as an aerosol spray, in a pump-dispenser bottle as a roll-on, in the form of thick creams distributed in tubes or a grille, in the form of wands (sticks), and may comprise ingredients generally used in products of this type and well known to those of skill in the art, provided that they do not interfere with the aluminum salt and the zinc gluconate described above.

The cosmetic deodorant compositions provided herein may optionally comprise at least one aqueous phase. They may be formulated as aqueous lotions, water-in-oil emulsions, oil-in-water emulsions, or as multiple emulsions such as oil-in-water-in-oil and water-in-oil-in-water triple emulsions. Such emulsions are known and described, for example, by C. F. Fox in "Cosmetics and Toiletries," November 1986, Vol.101, pages 101-112.

The aqueous phase of the compositions comprise water and generally at least one water-soluble or water-miscible solvent. Water-soluble and water-miscible solvents include short-chain monoalcohols, such as $C_1$-$C_4$ monoalcohols, for example ethanol and isopropanol; as well as diols and polyols, for example, ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, and sorbitol. For example, propylene glycol and glycerol may be used.

The antiperspirant compositions may optionally be anhydrous.

As used herein, the term "anhydrous" refers to a composition with a free or added water content of less than 3% by weight, for example with an added water content of less than 1% by weight, relative to the total weight of the composition.

The compositions may optionally comprise at least one water-immiscible organic liquid phase. This phase generally comprises at least one hydrophobic compound that renders the phase water-immiscible. The water-immiscible organic liquid phase is liquid (in the absence of a structuring agent) at room temperature (25° C.). The water-immiscible organic liquid phase generally comprises an oil or mixture of oils and comprises at least 80% of compounds with a vapor pressure not exceeding 4 kPa (30 mmHg) at 25° C.

The water-immiscible organic liquid phase may optionally comprise at least one volatile or non-volatile, silicone-based or hydrocarbon-based emollient oil. Suitable emollient oils include those described in U.S. Pat. Nos. 4,822,596 and 4,904,463.

As is known in the art, volatile silicones are room temperature. Volatile silicones include cyclic and linear volatile dimethylsiloxane silicones with chains comprising from 3 to 9 silicone-based residues. Cyclomethicones D4, D5, and D6 may be used.

As is known in the art non-volatile silicones are compounds with a low vapor pressure at room temperature. Non-volatile silicones include polyalkylsiloxanes, such as polyalkylsiloxanes, for example linear polydimethylsiloxanes and dimethicones, sold by Dow Corning under the name "Dow Corning 245 Fluid;" polyalkylarylsiloxanes, such as polymethylphenylsiloxanes sold by Dow Corning under the name "Dow Corning 556 Fluid;" and polyether and siloxane copolymer, for example, dimethicone copolyols.

Non-volatile emollient oils that may be used in the compositions include hydrocarbon-based derivatives; mineral oils; fatty alcohols; esters of $C_3$-$C_{18}$ alcohols with $C_3$-$C_{18}$ acids; esters of benzoic acid with $C_{12}$-$C_{18}$ alcohols and mixtures thereof; $C_2$-$C_6$ polyols, for example, glycerol, propylene glycol, and sorbitol; and polyalkylene glycol polymers.

The emollient oils may be present in the composition in an amount ranging from 1% to 50% by weight, for example, from 5% to 40% by weight, relative to the total weight of the composition.

The deodorant cosmetic compositions may further comprise at least one additional deodorant active agent, for example, bacteriostatic agents and bactericidal agents such as 2,4,4'-trichloro-2'-hydroxydiphenyl ether (Triclosan),2,4-dichloro-2'-hydroxydiphenyl ether, 3',4',5'-trichlorosalicylanilide, 1-(3',4'-dichlorophenyl)-3-(4'-chlorophenyl)urea (Triclocarban), and 3,7,11-trimethyidodeca-2,5,10-trienol (Farnesol); quaternary ammonium salts, for example, cetyltrimethylammonium salts and cetylpyridinium salts; chlorhexidine and salts thereof; diglyceryl monocaprate, diglyceryl monolaurate, and glyceryl monolaurate; and polyhexamethylene biguanide salts.

At least one suspension agent may be used to improve the homogeneity of the compositions. Suspension agents include hydrophobic-modified montmorillonite clays, for example, hydrophobic-modified bentonites and hectorites. Examples include stearalkonium bentonite (CTFA name, product of reaction of bentonite and the quaternary ammonium stearalkonium chloride), such as the commercial product sold under the name Tixogel MP 250 by Sud Chemie Rheologicals, United Catalysts Inc.; and the product disteardimonium hectorite (CTFA name, product of reaction of hectorite and of distearyldimonium chloride) sold under the name Bentone 38 or Bentone Gel by Elementis Specialities.

The suspension agents may be present in an amount ranging from 0.1% to 5% by weight, for example from 0.2% to 2% by weight, relative to the total weight of the composition.

The compositions may optionally further comprise at least one filler, such as an organic powder. Fillers that may be used in the compositions include organic powders. As used herein, the term "organic powder" means any solid that is insoluble in the medium at room temperature (25° C.).

Organic powders that may be used in the compositions include polyamide particles such as those sold under the name Orgasol by Atochem; polyethylene powders; microspheres based on acrylic copolymers, such as those made of ethylene glycol dimethacrylate/lauryl methacrylate copolymer, sold by Dow Corning under the name Polytrap; polymethyl methacrylate microspheres, sold under the name Microsphere M-100 by Matsumoto and under the name Covabead LH85 by Wackherr; ethylene-acrylate copolymer powders, for example, those sold under the name Flobeads by Sumitomo Seika Chemicals; expanded powders such as hollow microspheres and microspheres formed from a terpolymer of vinylidene chloride, of acrylonitrile and of methacrylate and sold under the name Expancel by Kemanord Plast under the references 551 DE 12 (particle size of about 12 µm and density of 40 kg/m3), 551 DE 20 (particle size of about 30 µm and a density of 65 kg/m 3) and 551 DE 50 (particle size of about 40 µm), and the microspheres sold under the name Micropearl F 80 ED by Matsumoto; powders of natural organic materials such as starch powders, for example, of corn starch, wheat starch, and rice starch, which may or may not be crosslinked, such as the starch powder crosslinked with octenylsuccinate anhydride, sold under the name Dry-Flo by National Starch; silicone resin microbeads such as those sold under the name Tospearl by Toshiba Silicone, for example, Tospearl 240; amino acid powders such as the lauroyllysine powder sold under the name Amihope LL-11 by Ajinomoto; particles of wax microdispersion, which have mean sizes of less than 1 µm, for example, ranging from 0.02 µm to 1 µm, and which comprise a wax or a mixture of waxes, such as the products sold under the name Aquacer by Byk Cera and Aquacer 520 (mixture of synthetic and natural waxes), Aquacer 514 and 513 (polyethylene wax), Aquacer 511 (polymer wax), the products sold under the name Jonwax 120 by Johnson Polymer (mixture of polyethylene wax and paraffin wax), and under the name Ceraflour 961 by Byk Cera (micronized modified polyethylene wax); and mixtures thereof.

The cosmetic compositions may also comprise cosmetic adjuvants chosen from waxes, softeners, antioxidants, opacifiers, stabilizers, moisturizers, vitamins, fragrances, bactericides, preserving agents, polymers, fragrances, thickeners, propellants, and any other ingredient usually used in cosmetics for this type of application.

Needless to say, a person of skill in the art can select optional additional compounds such that the advantageous properties intrinsically associated with the cosmetic compositions are not, or are not substantially, adversely affected by the envisaged addition.

Waxes include animal, fossil, plant, mineral, and synthetic waxes, for example, beeswaxes, carnauba wax, candelilla wax, sugar cane wax, Japan wax, ozokerites, montan wax, microcrystalline waxes, paraffins, silicone waxes, and resins.

The thickeners, which may be nonionic, include modified and unmodified guar gums and celluloses, such as hydroxypropyl guar gum and cetylhydroxyethylcellulose, silicas, for example, Bentone Gel MIO sold by NL Industries, and Veegum Ultra sold by Polyplastic.

The amounts of these various constituents that may be present in the cosmetic compositions are those conventionally used in deodorant compositions.

The compositions may optionally further comprise at least one other agent for structuring or gelling the water-immiscible organic liquid phase of the composition, such as linear solid fatty alcohols and/or waxes; fatty acids and salts thereof, for example, stearic acid, sodium stearate, and 12-hydroxystearic acid; dibenzylidene alditols (DBS); lanosterol; N-acylamino acid derivatives; di- and tricarboxylic acid derivatives, for example, alkyl-N,N'-dialkylsuccinamides, e.g., dodecyl-N, N'-dibutylsuccinamide; elastomeric polyorganosiloxanes such as those described in PCT Patent Application No. WO 97/44010.

The compositions according may also be pressurized and may be packaged in an aerosol device.

The present disclosure also provides aerosol devices comprising:
  (a) a container comprising a composition as defined above,
  (b) at least one propellant, and
  (c) a means for distributing the composition.

The propellants generally used in products of this type, which are well known to those skilled in the art, include, for example, dimethyl ether (DME) and volatile hydrocarbons such as n-butane, propane, and isobutane, and mixtures thereof, optionally with at least one chlorohydrocarbon and/or fluorohydrocarbon. Examples include the compounds sold by Dupont de Nemours under the names Freon® and Dymel®), for example, monofluorotrichloromethane, difluorodichloromethane, tetrafluorodichloroethane and 1,1-difluoroethane sold under the trade name Dymel 152 A by Dupont. Carbon dioxide, nitrous oxide, nitrogen, and compressed air may also be used as propellants.

The composition comprising the deodorant active agents and the propellants may be in the same compartment or in different compartments in the aerosol container. The concentration of propellant generally ranges from 5% to 95% by pressurized weight, for example from 50% to 85% by weight, relative to the total weight of the pressurized composition.

The distribution means, which forms a part of the aerosol device, generally comprises a distribution valve controlled by a distribution head comprising a nozzle via which the aerosol composition is vaporized. The container comprising the pressurized composition may be opaque or transparent. It may be made of glass, of polymeric material or of metal, optionally coated with a coat of protective varnish.

The present disclosure also provides cosmetic processes for treating human underarm odors, comprising applying to the underarm area an effective amount of a deodorant composition as defined above.

The invention is illustrated in greater detail by the examples described below. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

EXAMPLE 1

Comparison of the Deodorant Activity of the Zinc Gluconate/aluminum Salt Combination Relative to the Triclosan/aluminium Salt and Zinc Ricinoleate/aluminum Salt Combinations Protocol of the deodorant efficacy test Collections of underarm sweat were taken in a sauna from 6 volunteers; the samples of individual sweat were stored in ice for a few hours and were initially almost odorless. They were mixed together and divided into 1 ml aliquots. The active agents were added to the aliquots, which were then incubated in an oven at 37° C. After incubation for 24 hours, a panel of experts evaluated the intensity of the odor in comparison with a control sample: 1 ml of sweat incubated without an active agent. The intensity was evaluated on a scale ranging from 0 (no odor) to 4 (very strong odor).

The results below are expressed as a percentage of variation of the intensity of the odor in comparison with the control sweat sample (mean of the percentages of variation at T24h).

Δ = (odor intensity of the control sample − odor intensity of the sample with active agent) × 100 ÷ (odor intensity of the control sample)

| Active agents tested | Amount tested (mg AM/ml of sweat) | % of reduction in the intensity of the odor |
|---|---|---|
| ACH | 0.1 mg AM | −37% |
| (A) | 0.5 mg AM | −19% |
| (B) | 0.4 mg AM | −49% |
| (C) | 0.3 mg AM | −4% |
| ACH + (A) | 0.6 mg AM | −83% |
| ACH + (B) | 0.5 mg AM | −46% |
| ACH + (C) | 0.4 mg AM | −38% |

ACH: aluminum chlorohydrate (Micro Dry - Reheis)
(A): zinc gluconate (Govobio G Zn - SEPPIC)
(B): Triclosan (Ciba)
(C): zinc ricinoleate (Grillo Werke)

It was found that the zinc gluconate/aluminum salt combination (weight ratio: 5/1) led to a synergistic effect on reducing the intensity of the odor in contrast to the Triclosan/aluminum salt and zinc ricinoleate/aluminum salt combinations.

EXAMPLE 2

Microbiological Test: Sparingly Bactericidal Activity of Zinc Gluconate Compared with Triclosan Protocol:

The test described herein allowed a quantitative determination of the bactericidal activity of a composition on microorganisms under optimum growth conditions, i.e., *Corynebacterium xerosis* (Institut Pasteur collection No. 5216); *Staphylococcus hominis* (Institut Pasteur collection No. 8157) and *Brevibacterium epidermidis* (Institut Pasteur collection No. 102,110) microorganisms cultured on a gradient of tryptocasein soybean agar. On the day before the test, 32 g of tryptocasein soybean broth was placed in a pill bottle and incubated at 35° C. On the day of the test, 4 g of the test composition was added and the mixture was homogenized using a vortex mixer.

A growth control without product was prepared under the same conditions to ensure that the microorganisms were under favorable growth conditions throughout the test.

For the preparation of the inoculum, five days before the start of the test, two bacterial strains were subcultured on a suitable medium. They were incubated for 5 days at 35° C. On the day of the test, the slope was washed with approximately 9 ml of diluent. The suspension obtained had a titer of 108 microorganisms/ml (counting was performed). 4 ml of inoculum was introduced into the pill bottle, which corresponded to a content of 107 bacteria per gram of preparation. The pill bottle was placed in an incubator-shaker (35° C., 200 rpm).

After each contact time (2, 4, 6 and 24 hours), the contents of the pill bottle were homogenized using the vortex mixer. Tenfold dilutions were prepared. They were applied to the surface of agar Petri dishes (Eugon LT 100 medium). The Petri dishes were incubated for 6 to 7 days in an oven at 35° C.

The colonies on the dishes containing more than 20 and fewer than 200 colonies were counted.

| Identical results: | zero, |
|---|---|
| 1 log of reduction: | low, |
| 2 log of reduction: | moderate, |
| 3 log of reduction: | good, |
| >4 log of reduction: | excellent. |

Formulation 1, with zinc gluconate in accordance with the disclosure, and Formulation 2, with Triclosan in accordance with the prior art, were prepared, as shown below; the supports were chosen so as to be compatible with the deodorant active agent.

| Ingredients | Formulation 1 | Formulation 2 |
|---|---|---|
| Triclosan | — | 0.1 g |
| Zinc gluconate | 1 g | — |
| Polyethylene glycol 8 EO | 16.8 g | 6 g |
| Acrylic acid/$C_{10}$-$C_{30}$ alkyl acrylate crosslinked copolymer | — | 0.9 g |
| Pure sodium hydroxide | — | qs (pH = 7) |
| Microbiologically clean deionized water | 82.8 g | 93.0 g |

The bactericidal activity of formulations 1 and 2 with respect to the strains *Corynebacterium xerosis, Staphylococcus hominis* and *Brevibacterium epidermidis* were measured and compared to a formulation free of active agent (placebo). The results obtained are summarized in the following table:

| | Efficacy at 24 hours relative to the gel free of active agent Strains | | |
|---|---|---|---|
| Compositions | *Corynebacterium xerosis* (CIP 5216) | *Staphylococcus hominis* | *Brevibacterium epidermis* |
| Formulation 1 | zero | moderate | zero |
| Formulation 2 | excellent | — | — |

In formulation 1, the zinc gluconate used at a concentration 10 times higher than that of the Triclosan of formulation 2, had low or moderate antibacterial activity on the various strains tested. It thus had a substantially narrower spectrum of bactericidal activity than that of Triclosan and showed a greater respect for cutaneous flora.

EXAMPLES 3 AND 4

Deodorant Sticks

Formulation 3, according to Example 1.4 of patent application WO 01/99376, and formulation 4, in accordance with the disclosure, were prepared as shown below.

| Ingredients | Formulation 3 | Formulation 4 |
|---|---|---|
| Cyclopentasiloxane (DC245 - Dow Corning) | 23 g | 32 g |
| Hexyldecyl stearate (Eutanol G16S - Cognis) | 15 g | — |
| PPG-14 butyl ether (Ucon Fluid AP - Amerchol) | 5 g | 10 g |
| Hydrogenated castor oil (Cutina HR - Cognis) | 6 g | 4 g |
| Cetearyl alcohol (Lanette O - Cognis) | 8 g | — |
| Cetearyl alcohol/Ceteareth-30 80/20 (Sinnowax AO - Cognis) | 15 g | — |
| Talc | 8 g | 2 g |
| Aluminum chlorohydrate (Micro Dry - Reheis) | 20 g | 20 g |
| Zinc gluconate (Govobio G Zn-Seppic) | 0.1 g | 1 g |
| Stearyl alcohol | — | 14 g |
| PEG-8 distearate (PEG 400 distearate - Stearineries Dubois) | — | 2 g |
| $C_{12-15}$ alkyl benzoate (Finsolv TN - Witco) | — | 15 g |
|  | 100 | 100 |

The cyclopentasiloxane was heated to 65° C. The other ingredients were added one at a time while maintaining the temperature between 65 and 70° C. The mixture was homogenized (transparent solution) for 15 minutes. The two deodorant active agents and the talc were added. The resulting mixture was cooled to approximately 55° C., a few degrees above the thickening point of the mixture, and cast into sticks. The sticks were placed at 4° C. for 30 minutes.

The deposits of white residue of the sticks of Examples 3 and 4 after application were measured according to the test described below.

Protocol

The measurements were performed using a Minolta CR300 machine. The products were applied in a homogeneous manner until approximately 1 g of product per 40 cm2 was obtained on a Canson mid-tint sheet black paper. The measurement was performed immediately after application. An average of two measurements was reported.

The change in L was measured as follows: $\Delta L = L^*product - L^*reference$.

An L*reference of 19.45 was used for the Canson mid-tint sheet black paper.

A ΔL of greater than or equal to 35 for a product is indicative of a cosmetically unacceptable amount of whitening.

The results obtained are summarized in the following table:

| Composition | ΔL |
|---|---|
| Formulation 3 | 35 |
| Formulation 4 | 6 |

It was found that composition 3 (according to the prior art) containing a zinc gluconate/aluminum chlorohydrate combination in a 1/200 ratio produced a high level of white residue on the substrate, whereas composition 4 produced very little white residue, comparable with deodorant sticks currently on the market, such as the commercial products "Lady Speed Stick—Clean Glide" from Colgate and "Secret Clear Dry" from Procter & Gamble.

EXAMPLE 5

Roll-on (Emulsion)

| Phase | Ingredients | Formulation 5 |
|---|---|---|
| A | Aluminum chlorohydrate (50% solution) (Chlorhydrol 50% USP) | 40 g |
|  | Zinc gluconate (Govobio G Zn-Seppic) | 2 g |
| B | Steareth-21 (Brij 721 - ICI) | 2 g |
|  | Steareth-2 (Brij 2 - ICI) | 2 g |
|  | Steareth-5 Stearate | 1 g |
|  | PPG-15 stearyl ether (Arlamol E - ICI) | 1.5 g |
|  | Cyclopentasiloxane (DC245 - Dow Corning) | 3.5 g |
| C | Water | 48 g |
|  |  | 100 g |

Phases (B) and (C) were heated separately to 70° C. then mixed together using a Turrax stirrer for 5 minutes and then cooled to 55° C. with paddle stirring. Phase (A) was added slowly while stirring. The mixture was homogenized for 1 to 3 minutes, then cooled to 35° C. with stirring. The formulation was stable for 2 months at 45° C.

The amount of white residue was measured according to the test as described in Examples 3 and 4. A ΔL equal to 2 was obtained.

EXAMPLE 6

Non-Aerosol Spray (Emulsion Obtained by Phase Inversion)

| Ingredients | Formulation 6 |
|---|---|
| Aluminum chlorohydrate (50% solution) (Chlorhydrol 50% USP) | 20 g |
| Zinc gluconate (Govobio G Zn-Seppic) | 3 g |
| Cetearyl isononanoate (and) Cetearyl alcohol (and) Ceteareth-20 (and) Glycerin (and) Glyceryl stearate (and) Ceteareth-12 (and) cetyl palmitate (Emulgade CM - Cognis) | 15 g |
| Water | 62 g |
|  | 100 g |

The gluconate was dissolved in water and Emulgade CM was added with moderate stirring. The aluminum salt solution was added with moderate stirring. The formulation was stable for 2 months at 45° C. The amount of white residue was measured according to the test described in Examples 3 and 4. A ΔL equal to 0 was obtained.

EXAMPLE 7

Aerosol

| Ingredients | Formulation 7 |
| --- | --- |
| Stearalkonium Bentonite (Tixogel MP 250 - Sud Chemie Rheologicals United Catalysts Inc.) | 0.5 g |
| Aluminum chlorohydrate (Micro Dry - Reheis) | 7 g |
| Zinc gluconate (Govobio G Zn-Seppi) | 0.5 g |
| $C_{12-15}$ alkyl benzoate (Finsolv TN - Witco) | 3 g |
| Isobutane | 80 g |
| Triethyl citrate (Citroflex-Morflex) | 1 g |
| Isopropyl palmitate | 1 g |
| Cyclopentasiloxane (DC245 - Dow Corning) | 7 g |
| | 100 g |

The solvents and the hydrophobic-modified clay were added and the mixture was stirred using a Turrax stirrer until homogenized. The aluminum salt (antiperspirant) and the zinc gluconate were then added with continued stirring. The propellant was then introduced in a conventional manner. The level of white residue was measured according to the test described in Examples 3 and 4. A ΔL equal to 4 was obtained for formulation 7.

What is claimed is:

1. A composition comprising:
   zinc gluconate, and
   at least one antiperspirant aluminum salt; wherein the zinc gluconate/antiperspirant aluminum salt weight ratio ranges from 1/100 to 10/1.

2. The composition according to claim 1, wherein zinc gluconate/antiperspirant aluminum salt weight ratio ranges from 1/20 to 5/1.

3. The composition according to claim 1, wherein the at least one antiperspirant aluminum salt is chosen from aluminum halohydrates, aluminum zirconium halohydrates, and complexes of zirconium hydroxychloride and of aluminum hydroxychloride with an amino acid.

4. The composition according to claim 3, wherein the at least one antiperspirant aluminum salt is chosen from aluminum chlorohydrate in activated or unactivated form, aluminum chlorohydrex, aluminum chlorohydrex polyethylene glycol complex, aluminum chlorohydrex propylene glycol complex, aluminum dichlorohydrate, aluminum dichlorohydrex polyethylene glycol complex, aluminum dichlorohydrex propylene glycol complex, aluminum sesquichlorohydrate, aluminum sesquichlorohydrex polyethylene glycol complex, aluminum sesquichlorohydrex propylene glycol complex, and aluminum sulfate buffered with sodium aluminum lactate.

5. The composition according to claim 3, wherein the at least one antiperspirant aluminum salt is chosen from aluminum zirconium octachlorohydrate, aluminum zirconium pentachlorohydrate, aluminum zirconium tetrachlorohydrate, and aluminum zirconium trichlorohydrate.

6. The composition according to claim 3, wherein the at least one antiperspirant aluminum salt is a complex of zirconium hydroxychloride and aluminum hydroxychloride with glycine.

7. The composition according to claim 6, wherein the at least one antiperspirant aluminum salt is chosen from aluminum zirconium octachlorohydrex glycine, aluminum zirconium pentachlorohydrex glycine, aluminum zirconium tetrachlorohydrex glycine, and aluminum zirconium trichlorohydrex glycine complexes.

8. The composition according to claim 1, wherein the at least one antiperspirant aluminum salt is aluminum chlorohydrate in an activated or unactivated form.

9. The composition according to claim 1, wherein the at least one antiperspirant aluminum salt is present in an amount ranging from 0.5% to 25% by weight relative to the total weight of the composition.

10. The composition according to claim 1, wherein the zinc gluconate is present in an amount ranging from 0.1% to 10% by weight relative to the total weight of the composition.

11. The composition according to claim 10, wherein the zinc gluconate is present in an amount ranging from 0.1% to 7% by weight relative to the total weight of the composition.

12. The composition according to claim 1, wherein the composition is in a form chosen from a lotion;, a cream or a fluid gel distributed as an aerosol spray, a pump-dispenser bottle, or a roll-on; a cream distributed in a tube or grille; a gel distributed in a tube or grille; and a stick.

13. The composition according to claim 1, further comprising at least one aqueous phase.

14. The composition according to claim 13, wherein the composition is in the form of an aqueous lotion, a water-in-oil emulsion, an oil-in-water emulsion, or a multiple emulsion.

15. The composition according to claim 13, wherein the aqueous phase comprises water and at least one water-soluble or water-miscible solvent.

16. The composition according to claim 15, wherein the at least one water-soluble or water-miscible solvent is chosen from $C_1$-$C_4$ monoalcohols, diols and polyols.

17. The composition according to claim 1, wherein the composition is anhydrous.

18. The composition according to claim 1, further comprising at least one water-immiscible organic liquid phase.

19. The composition according to claim 18, wherein the water-immiscible organic liquid phase comprises at least one volatile or non-volatile silicone-based or at least one volatile or non-volatile hydrocarbon-based emollient oil.

20. The composition according to claim 19, wherein the emollient oils are present in an amount ranging from 1% to 50% by weight relative to the total weight of the composition.

21. The composition according to claim 20, wherein the emollient oils are present in an amount ranging from 5% to 40% by weight relative to the total weight of the composition.

22. The composition according to claim 18, further comprising at least one agent for structuring or gelling the water-immiscible organic liquid phase.

23. The composition according to claim 1, further comprising at least one additional deodorant active agent.

24. The composition according to claim 23, further comprising at least one bacteriostatic agents or bactericidal agent.

25. The composition according to claim 1, further comprising at least one suspension agent.

26. The composition according to claim 1, further comprising at least one organic powder.

27. The composition according to claim 1, further comprising at least one cosmetic additive chosen from waxes, softeners, antioxidants, opacifiers, stabilizers, moisturizers, vitamins, fragrances, bactericides, preserving agents, polymers, fragrances, thickeners, and propellants.

28. An aerosol device comprising:
(a) a container comprising a deodorant composition comprising zinc gluconate and at least one antiperspirant aluminum salt; wherein the zinc gluconate/antiperspirant aluminum salt weight ratio ranges from 1/100 to 10/1;
(b) at least one propellant; and
(c) a means for distributing the deodorant composition.

29. A cosmetic process for treating human underarm odor, comprising applying to the underarm area an effective amount of to treat odor of a composition comprising:
(a) zinc gluconate, and
(b) at least one antiperspirant aluminum salt;
wherein the zinc gluconate/antiperspirant aluminum salt weight ratio ranges from 1/100 to 10/1.

* * * * *